(12) United States Patent
Choi et al.

(10) Patent No.: US 7,618,661 B2
(45) Date of Patent: Nov. 17, 2009

(54) PROCESS FOR PREPARATION OF RHUS VERNICIFLUA EXTRACTS HAVING EXCELLENT ANTI-CANCER ACTIVITY AND ANTI-CANCER PHARMACEUTICAL COMPOSITION CONTAINING THE SAME

(75) Inventors: Won-Cheol Choi, Incheon (KR); Sang-Jae Park, Yongin-Si (KR); Sung-Pil Kwon, Seoul (KR)

(73) Assignee: Azi Co., Ltd., Chuncheon-Si Gangwon-Do (KR)

( * ) Notice: Subject to any disclaimer, the term of this patent is extended or adjusted under 35 U.S.C. 154(b) by 290 days.

(21) Appl. No.: 11/719,292

(22) PCT Filed: Apr. 28, 2006

(86) PCT No.: PCT/KR2006/001601
§ 371 (c)(1),
(2), (4) Date: May 14, 2007

(87) PCT Pub. No.: WO2007/049846
PCT Pub. Date: May 3, 2007

(65) Prior Publication Data
US 2009/0053330 A1    Feb. 26, 2009

(30) Foreign Application Priority Data
Oct. 25, 2005   (KR) .................. 10-2005-0100578

(51) Int. Cl.
*A01N 65/00* (2006.01)
(52) U.S. Cl. .................................. 424/725
(58) Field of Classification Search ............... None
See application file for complete search history.

(56) References Cited

U.S. PATENT DOCUMENTS

2004/0110847 A1* 6/2004 Wu et al. ................. 514/734
2005/0089980 A1* 4/2005 Kruus et al. ............... 435/189
2005/0210744 A1* 9/2005 Watanabe et al. ........ 47/58.1 LS

FOREIGN PATENT DOCUMENTS

| JP | 11-049693 | 2/1999 |
|---|---|---|
| KR | 1019980076449 | 11/1998 |
| KR | 1020010111159 | 12/2001 |
| KR | 1020040027794 | 4/2004 |
| KR | 1020040079397 | 9/2004 |

OTHER PUBLICATIONS

Lee, J.C. "Flavonoid fraction purified from Rhus verniciflua Stokes . . . " Nat. Prod. Sci. 2004, pp. 74-79, vol. 10, No. 2, Chonbuk Nat'l Univ., Chonju, KR.
Kim, M.J. et al. "Anticancer and antioxidant activity of allergen-removed . . . " Korean J. Medic. Crop Sci. 2002, pp. 288-293, vol. 10, No. 4, Kangwon Nat'l Univ., Chuncheon, KR.
Kim, H.D. et al. "Accelerating effect of TNF-alpha on the Rhus . . . " Nat. Prod. Sci. 2005, pp. 45-49, vol. 11, No. 1, Chonbuk Nat'l Univ., Chonju, KR.
Lim, K.T. et al. "Bioactive utility of the extracts form Rhus . . . " Korean J. Food Sci. Technol. 1999, pp. 238-245, vol. 31, No. 1, Chonnam Nat'l Univ., Kwangju city, KR.
Lee, J.C. et al. "Effects of Rhus verniciflua Stokes(RVS) . . . " J. Toxicol. Public Health, 1999, pp. 169-175, vol. 15, No. 2, Chonnam Nat'l Univ., Kwangju, KR.
Lee, J.C. et al. "Extacts from Rhus verniciflua Stokes is capable . . . " Food Chem. Toxicol. 2004, pp. 1383-1388, vol. 42, No. 9, Chonbuk Nat'l Univ., Chonju, KR.

* cited by examiner

*Primary Examiner*—Michael V Meller
(74) *Attorney, Agent, or Firm*—IPLA P.A.; James E. Bame

(57) ABSTRACT

Provided is a process for preparation of a *Rhus verniciflua* extract, comprising extracting allergen-removed *Rhus verniciflua* with a soluble solvent, thereby obtaining an extract, subjecting the thus-obtained extract to ultrafiltration to remove high-molecular weigh substances, concentrating and drying the resulting material, thereby obtaining extract powder and irradiating far-infrared to the extract powder, thereby improving anti-cancer activity. The *Rhus verniciflua* extract prepared according to the process of the present invention exhibits superior anti-cancer activity.

5 Claims, No Drawings

PROCESS FOR PREPARATION OF RHUS VERNICIFLUA EXTRACTS HAVING EXCELLENT ANTI-CANCER ACTIVITY AND ANTI-CANCER PHARMACEUTICAL COMPOSITION CONTAINING THE SAME

FIELD OF THE INVENTION

The present invention relates to a process for preparation of a *Rhus verniciflua* extract having excellent anti-cancer activity and a pharmaceutical composition containing the same. More specifically, the present invention relates to a process for preparation of a *Rhus verniciflua* extract comprising extracting allergen-free *Rhus verniciflua* with solvents including water and ethanol, subjecting the extract to ultra-filtration to remove high-molecular weight substances, concentrating and drying the resulting filtrate, and irradiating far-infrared to the product, thereby significantly improving anti-cancer activity, and an anti-cancer pharmaceutical composition containing such a *Rhus verniciflua* extract as an active ingredient.

BACKGROUND OF THE INVENTION

The lacquer tree, *Rhus verniciflua* is a deciduous broadleaf tree belonging to the family Anacardiaceae, and the sap thereof is also called a lacquer paint or Lacca Sinica Exsiccata (dried resin of *Rhus verniciflua*) which is generally used for industrial and medicinal purposes. Particularly, in herbal medicine therapy and folk therapy, *Rhus verniciflua* has been used as a medicinal material for various applications including treatment of alcohol poisoning, removal or alleviation of fever, expulsion of intestinal parasites, treatment of malaria, and removal or alleviation of abdominal pain, menstrual abdominal pain and constipation, and has also been used as a folk medicine and a healthy food by ingestion of chicken boiled with lacquer tree (Tae-Jung Kim, Korea resource plants (1996), vol. II, pp. 294, published by Seoul National University Press, Seoul, Korea). A variety of research and study has been reported on physiological activity of *Rhus verniciflua* extracts. For example, it was reported that *Rhus verniciflua* extracts have antibacterial action, and antioxidant action of flavonoid components and urushiol components found in the sap of the plants (Korean Journal of Food Science & Technology, 31:855-6.3; and Korean Journal of Pharmacognosy 31:345-50). Cytotoxic effects of urushiol components on cancer cells were also reported (Arch. Pharm. Res. 22:638-41 (2000)).

Despite its various physiological activities, *Rhus verniciflua* has suffered from many limitations in applications thereof for a long period of time, due to the allergy-inducing potential. Owing to many efforts, it was elucidated that the main allergy-inducing agent (allergen) in *Rhus verniciflua* is urushiol, which has brought about a great deal of approaches and methods to remove urushiol. For example, there may be exemplified a method involving heat treatment of *Rhus verniciflua*, a method involving solvent extraction of *Rhus verniciflua*, followed by standing of the extract at a low temperature, and a method involving treatment of *Rhus verniciflua* with oxygen.

The majority of conventional arts relating to *Rhus verniciflua* and utilization thereof published hitherto is directed to methods concerning a technology of removing allergenicity, methods concerning pharmacological efficacy of urushiol known as an allergen, pharmaceutical compositions containing the same and preparation thereof, and methods concerning separation and purification of an allergenicity-free *Rhus verniciflua* extract and pharmacological efficacy thereof.

On the other hand, *Rhus verniciflua* contains large quantities of antioxidant substances. For example, In-Won Kim, et al have reported isolation of antioxidant substances from *Rhus verniciflua* bark extracts (Korean J. Food Sci. Technol. 31(3), 855-63 (1999)), and Kye-Taek Lim, et al. have reported that application of a fractionated ethanol extract derived from *Rhus verniciflua* to brain cells of rats results in strong antioxidant activity (Korean J. Food Sci. Technol. 29, 1248-54 (1997)). Hyung-Jin Jeong, et al. have reported antioxidant power of *Rhus* species and fractionation method thereof (Korean J. plant. Res. 14(3), 220-8 (2001)). In addition, J.-C. Lee, et al. have reported that the fraction of *Rhus verniciflua* extract isolated and purified using a silica column exhibits inhibitory effects on the growth of human blood cancer cells (Food and Chemical Technology 42, 1383-88 (2004)). Jung-Chae Lee, et al. have reported a fraction having antioxidant and antimicrobial effects, derived from an ethanol extract of *Rhus verniciflua* (Food Sci. Biotechnol. 9(3), 139-45 (2000)). Won-Sig Choi, et al. have reported antioxidant effects of components isolated and purified from a methanol extract fraction of *Rhus verniciflua* and also reported that such a fraction has no significant activity in a cytotoxic test on cancer cells (J. Korean Soc. Agric. Chem. Biotechnol. 45(3), 168-72 (2002)). Kye-Taek Lim has compared and reported preventive effects of hepatocyte apoptosis between a water extract and ethanol extract of *Rhus verniciflua* (Agric. Chem. Biotechnol. 45(4), 173-9 (2002)). Won-Kyung Cheon, et al. have reported methanol extraction of *Rhus verniciflua* bark and anti-obesity effects of the extract on obesity-induced mice (Korean Journal of Pharmacognosy vol. 3494, 339-43 (2003)).

Further, as conventional arts directed to the anti-cancer activity of the *Rhus verniciflua* extract, Korean Patent Application Nos. 1997-00013163 and 1997-0004193 disclose anti-cancer compositions containing urushiol components. Korean Patent No. 0257448 proposes an anti-cancer composition containing fustin, fisetin, sulfuretin and butein, which were obtained by purification of the *Rhus verniciflua* extract using a silica column. Korean Patent No. 0251526 proposes an anti-cancer composition containing urushiol compounds as main ingredients. Korean Patent Application No. 2002-0018186 proposes *Rhus verniciflua* extracts having antioxidant effects and apoptosis-preventive effects by allowing ethanol extracts of *Rhus verniciflua* to stand for some time at a low temperature. Korean Patent Application No. 2002-0071464 proposes therapeutics for treating liver diseases, utilizing *Rhus verniciflua* extracts. Korean Patent Application No. 2001-0004700 proposes anti-cancer effects of drugs by light-induced ripening and use of an anti-cancer drug utilizing *Rhus verniciflua* extracts.

The majority of the above-mentioned conventional arts proposes anti-cancer drugs utilizing extracts containing urushiol, fustin, fisetin, sulfuretin, butein, caffeic acid, gallic acid and the like as the main components, by extracting *Rhus verniciflua* with a solvent including water and purifying the extract via various methods such as column.

However, despite known antioxidant characteristics and anti-cancer activity of *Rhus verniciflua* extracts, *Rhus verniciflua* extracts proposed in the above-mentioned conventional arts cannot exert desired levels of anti-cancer activity, thus resulting in failure of practical application thereof as an anti-cancer drug.

SUMMARY OF THE INVENTION

Therefore, the present invention has been made to solve the above problems and other technical problems that have yet to be resolved.

That is, a first object of the present invention is to provide a process for preparation of a *Rhus verniciflua* extract having excellent anti-cancer activity by a simplified process.

A second object of the present invention is to provide a pharmaceutical composition exerting excellent anti-cancer effects on various cancers, which is prepared by the above process.

DETAILED DESCRIPTION OF PREFERRED EMBODIMENTS

In accordance with an aspect of the present invention, the above and other objects can be accomplished by the provision of a process for preparation of a *Rhus verniciflua* extract, comprising:

(a) extracting allergen-removed *Rhus verniciflua* with a soluble solvent, thereby obtaining an extract;

(b) subjecting the thus-obtained extract to ultrafiltration to remove high-molecular weigh substances, concentrating and drying the resulting material, thereby obtaining extract powder; and (c) irradiating far-infrared to the extract powder, thereby improving anti-cancer activity.

As will also be confirmed through Examples which will described hereinafter, the *Rhus verniciflua* extract obtained according to the process of the present invention exerts significantly high anti-cancer activity, as compared to any other conventional *Rhus verniciflua* extracts.

As to step (a), removal of allergens from *Rhus verniciflua* may be carried out by a variety of methods known in the art and preferably by the method disclosed in Korean Patent No. 0504160, assigned to the present applicant, the disclosure of which is incorporated by reference herein in its entirety.

Then, the thus allergen-free *Rhus verniciflua* may be broken into chips, powder or sawdust and then subjected to solvent extraction.

Preferably, solvent extraction may be carried out using water and ethanol as soluble solvents.

In one preferred embodiment, an excessive amount of water as a first solvent is added to *Rhus verniciflua*, thereby obtaining a water extract, and an excessive amount of dilute ethanol as a second solvent is added to the *Rhus verniciflua* residues left after the first extraction, thereby obtaining an ethanol extract. Thereafter, the water extract and the ethanol extract may be combined to obtain a mixed extract.

Water, used as the first solvent, deeply penetrates into the inside of *Rhus verniciflua* chips, sawdust and the like and serves to extract water-soluble components. The extraction temperature is preferably in the range of 60 to 110° C. When the extraction temperature is lower than 60° C., it will take a long time for water to penetrate into the inside of *Rhus verniciflua* chips or sawdust, thus resulting in decrease of extraction efficiency. In contrast, when the extraction temperature is higher than 110° C., components of the extract may be undesirably destroyed or altered due to excessively high temperatures. In order to facilitate water penetration upon extraction, the inside of the extraction vessel may also be pressurized to 0.6 to 1.0 atm, by air or steam. In this case, a relative atmosphere exceeding 1.0 atm may result in increased operational hazards and increased production costs of facilities to withstand high pressure, due to excessively high pressure.

In order to dissolve out soluble components, the extraction solvent is preferably used in a 5 to 20-fold amount based on the weight of the raw material, thus meaning that 5 to 20 L of the solvent is added relative to 1 kg of *Rhus verniciflua* chips or sawdust. If extraction water is used in less than 5-fold addition amount, it is impossible to obtain a sufficient degree of extract. In contrast, if the amount of extraction water added is greater than 20-fold, the subsequent concentration step disadvantageously requires excessive time and costs. In addition, the extraction time is suitably in a range of 3 to 24 hours. Generally, since the higher extraction temperature may decrease the extraction time while the lower extraction temperature increases the extraction time, extraction at 60° C. is typically carried out for 24 hours. When the extraction time is longer than 24 hours, it is impossible to achieve improvement in an extraction yield, relative to additional time invested. The extraction time of less than 3 hours may lead to a decrease in an extraction yield.

For second extraction by ethanol as a second solvent, preferably, dilute ethanol having a 40 to 50% (v/v) ethanol concentration is added to the *Rhus verniciflua* residues left after the first extraction with water, in a 5 to 10-fold amount of the weight of initial *Rhus verniciflua*, followed by extraction at 60 to 70° C. for 3 to 10 hours.

Determining the ethanol concentration to the above range is because a yield of *Rhus verniciflua* extract is highest and non-water soluble, pharmacologically active substances are dissolved well at that concentration range. Generally, even though hydrophobic components are readily soluble in high-concentration ethanol, additional extraction by dilute ethanol after first extraction of water-soluble components with water, as described above, enables deep penetration of the solvent into the xylem of *Rhus verniciflua* during the first extraction process, thereby easily dissolving and extracting soluble components. High-concentration ethanol makes it difficult to achieve large-scale application and requires careful attention and expensive facility, but the above range of ethanol concentration is a concentration that can be easily handled and does not require installation of additional expensive facilities. In addition, upon extraction of active ingredients, the extraction yield was very high, more than 99%.

The temperature upon ethanol extraction is, taking into consideration the use of ethanol, set to the range of 60 to 70° C. which is lower temperature as compared to that of water extraction and this is intended to reduce operational risk factors.

In this manner, after first extraction by water and second extraction by dilute ethanol, two extracts may be combined to thereby obtain a mixed extract.

In connection with step (b), when the mixed extract obtained in step (a) is allowed to stand at 20 to 35° C. for 2 to 4 days, fine brown precipitates are formed. The thus-formed precipitates are generally high-molecular weight polysaccharides and it is preferred to remove them by microfiltration prior to concentration. Microfiltration may be performed using, for example a filter having a pore size of 0.45 μm.

The thus-obtained microfiltrate is subjected to ultrafiltration as described above, thereby removing high-molecular weight substances. Ultrafiltration is performed using a filtration membrane having a pore size significantly smaller than that of microfiltration, and it is possible to adjust the pore size of the filtration membrane depending upon molecular weight sizes of substances to be filtered.

A molecular weight cut-off value of the membrane used in ultrafiltration is preferably more than 500,000. Therefore, on the basis of 500,000 MW, it is possible to obtain a filtrate of components having a molecular weight of less than 500,000 which passes through the ultrafiltration membrane while removing components having a molecular weight of more than 500,000. Here, substances having a molecular weight of more than 500,000 are minimally absorbed into the body upon practical uptake and serve only as dietary fibers. Therefore, in order to enhance pharmacological efficacy, non-essential components having a molecular weight of more than 500,000 are screened and removed by the ultrafiltration membrane, on the basis of 500,000 MW.

The filtrates obtained by ultrafiltration may be concentrated in vacuo to 20 to 30 Bx and freeze-dried to obtain a product as brown or light brown powder. From experimental results performed by the inventors of the present inventions, the yield was 4 to 12% (w/w).

In connection with step (c), when far-infrared was irradiated to the *Rhus verniciflua* extract powder obtained as above, it was surprisingly confirmed that anti-cancer activity is significantly increased.

Far-infrared, a part of the spectrum of light emanating from the sun and discovered by German astronomer F. W. Herschel, is an electromagnetic wave having a wavelength longer than visible light but shorter than microwave and has a wavelength of 0.76 to 1,000 μm. Every object necessarily emits a particular wavelength if it contains heat. Far-infrared radiators emanating such infrared light serve as both radiator and absorber. Light with a wavelength of more than 4 μm among infrared is called far-infrared, which absorbs the temperature within the room temperature range and is emitted in the form of light energy converted to far-infrared. Advantages of far-infrared radiation exhibited upon the use of lumber in residential environment were stated for the first time by Lee, et al (Proceedings of International Furniture Symposium. 1-23, 1996). Wha-Hyung Lee has investigated and reported emissivity of far-infrared between various species of trees in Korea, with a result showing a similar degree of emissivity therebetween (J. of Korean Wood Sci. & Tech 33(1); 17-20 (2005)). Such far-infrared is a form of light energy and has various effects on the human body, objects, foodstuffs and the like. For example, Korean Patent Application No. 2001-0004700 discloses use of far-infrared as a light-induced ripening means of foodstuffs.

In the present invention, improving anti-cancer activity of the *Rhus verniciflua* extract powder via radiation of far-infrared may be achieved by various far-infrared treatment systems.

In one preferred embodiment, the far-infrared treatment system is comprised of a light source positioned at the uppermost part; a light-absorbing/heat-emitting layer having a thickness of 0.5 to 1 cm, absorbing lights from the light source and emitting heat, and being composed of charcoal powder having a 100-mesh size; a far-infrared radiating layer having a thickness of 0.5 to 1 mm, located underneath the light-absorbing/heat-emitting layer and composed of *Rhus verniciflua* dried in the shade; and a *Rhus verniciflua* extract powder layer having a thickness of 2 to 10 mm, located at a predetermined distance spaced away from the far-infrared radiating layer and sealed by a transparent substrate under inert atmosphere.

The light source may be natural light or an artificial light source. The artificial light source that can be used in the present invention includes, for example electric-light bulbs for irradiation of far-infrared, infrared and the like.

Where natural light is used as the light source, a glass substrate having a thickness of 2 to 10 mm may be further mounted over the light-absorbing/heat-emitting layer. In order to concentrate light from the light source, the glass substrate may use a convex lens instead of a flat glass, and concentrate natural light which in turn provides intense heat to black oak charcoal underneath the glass substrate. Upon using the convex lens, the temperature of the black oak charcoal located thereunder increases up to 60 to 120° C., due to concentrated light. When the thickness of glass is excessively thin, i.e. 2 to 10 mm, it is difficult to handle it. In contrast, if the thickness of glass is thicker than 10 mm, transmissivity of light becomes low. The spaced distance between the glass substrate and light-absorbing/heat-emitting layer is in the range of 3 to 20 cm, which is intended to concentrate sufficient amounts of light and thereby increase the temperature of the charcoal.

As the charcoal powder constituting the light-absorbing/heat-emitting layer, black oak charcoal powder may be preferably used. Charcoal powder having a size passing through the 100 mesh screen is employed. The larger sized charcoal particles leads to the lower absorption of light. The excessively smaller sized charcoal particles leads to difficulty of handling due to scattering of fine powder.

When the thickness of the light-absorbing/heat-emitting layer is excessively thick, it takes a long period of time to transfer heat to the far-infrared radiating layer thereunder. In contrast, when the thickness of the light-absorbing/heat-emitting layer is excessively thin, this undesirably results in failure to provide sufficient amount of heat emission.

Shade-dried *Rhus verniciflua* constituting the far-infrared radiating layer is preferably included in the form of fine powder or thin plate-like material. The thickness of the far-infrared radiating layer exceeding 1 mm undesirably results in deterioration of far-infrared emissivity.

*Rhus verniciflua* emits far-infrared via receipt of heat from charcoal which has absorbed sufficient amounts of heat. Here, as measured by FT-IR, the far-infrared emissivity of *Rhus verniciflua* at a temperature of 40 to 50° C. was more than 90% within the region of 5 to 20 μm wavelength. This result means that 90% of heat absorbed from charcoal was emitted in the form of far-infrared from *Rhus verniciflua*.

The *Rhus verniciflua* extract powder layer is disposed at the lower part of the far-infrared radiating layer, by spreading *Rhus verniciflua* extract powder on a container made of a transparent substrate such as glass, vinyl or the like and filling the inside thereof with inert gas such as nitrogen.

The *Rhus verniciflua* extract powder, which was processed to form the powder after concentration, is evenly spread to a thickness of 2 to 10 mm in an airtight container made of glass or vinyl through which light readily passes. Thereafter, nitrogen is injected to replace gases present in the airtight container which is then completely sealed to avoid contact with oxygen environment.

The treatment time in the above far-infrared treatment system may be preferably within the range of 1 to 24 hours. Far-infrared treatment exceeding 24 hours does not directly affect physical properties or efficacy of the *Rhus verniciflua* extract powder, and is undesirable taking into consideration efficiency of standard procedures. Further, far-infrared treatment of more than 48 hours was confirmed to give rise to occurrence of partial melting of the extract powder due to excessive heat.

Upon using the electric-light bulbs for irradiation of far-infrared or infrared as the artificial light source, 100 to 200 W bulbs may be used. Those having a greater power range may result in excessive heat generation and as a result, quality deterioration. Whereas, although natural light as the light source is advantageous in that it exhibits a lower risk of overheating as compared to the artificial light source and it is natural heat source, but it suffers from disadvantages in that it takes a long period of time to provide sufficient heat and it is impossible to take advantage of sunlight after sunset.

Irradiation of far infrared to the *Rhus verniciflua* extract basically not only activates active ingredients contained in the extract, but also serves to decompose high-molecular weight substances, thereby enhancing absorptiveness of the human body. Upon irradiation of far infrared to the *Rhus verniciflua* extracts, the difference in constituent components therebetween was within the range of analytical error, and there was some difference in colors ranging from dark brown to dark yellow.

In accordance with another aspect of the present invention, there is provided a *Rhus verniciflua* extract having anti-cancer activity, prepared by the above-mentioned method.

In order to analyze functional components of the *Rhus verniciflua* extract, 10% (w/v) *Rhus verniciflua* extract was dissolved in water, and the resulting solution was microfiltered through a filter paper having a pore size of 1 μm. Then, chloroform was added to the resulting filtrate in a volume ratio of 1:1, and the mixture was vigorously mixed and subjected to layer separation, thereby obtaining a lower chloroform layer. Ethyl acetate was added to the aqueous layer and the resulting mixture was then vigorously mixed. The mixture was subjected to layer separation, thereby separating the upper ethyl acetate layer and obtaining a ethyl acetate fraction. The ethyl acetate fraction was concentrated and dissolved to a 10% (w/v) solid concentration in methanol. The resulting solution was loaded on a silica column packed with silica having a 70 to 230 mesh size. The lower layer of a mobile phase composed of chloroform/methanol/water (70:21:9) was separated and developed with a mobile phase, thereby obtaining 5 fractions. Two of 5 fractions were loaded again on a column packed with reverse phase silica (C18) and developed with a mobile phase of methanol/water (65:35), thereby obtaining 5 fractions. Fustin and fisetin were isolated and purified from those fractions, and identified using standard materials purchased from Sigma.

As a result of component analysis, the *Rhus verniciflua* extract of the present invention was shown to basically contain 10 to 30% (w/w) fustin, 2 to 15% (w/w) fisetin and 15 to 45% (w/w) resin, and other components. Analysis of fustin and fisetin was performed in accordance with a flavonoid analysis method using HPLC. In addition, the resin is not a single material from the standpoint of characteristics of components thereof, and therefore a component that is soluble in ethanol but is non-soluble in water was taken as a standard. It is commonly known that the main components of the resin are tannins and that they exhibit difference in the composition thereof depending upon species of trees. The resin as used herein refers to a fraction having a molecular weight of less than 500,000, and is obtained by dissolving the *Rhus verniciflua* powder in ethanol with purity of 95% (v/v), filtering insoluble components, removing ethanol by evaporation, adding water thereto to remove water-soluble components, and drying the remaining solids. Significant variation in the composition of the *Rhus verniciflua* extract is due to the presence of some deviation resulting from the age and harvest time of trees, growing areas, parts to be harvested and the like.

It has been conventionally known to date that anti-cancer effects of the *Rhus verniciflua* extract are due to flavonoid substances contained in the extract, and particularly, to the best of our knowledge, there is yet no report showing the evidence that the resin from the *Rhus verniciflua* is associated with anti-cancer activity. However, the inventors of the present inventions have taken notice of the resin from the *Rhus verniciflua* extract as the causative agent exerting anti-cancer activity thereof. As can also be confirmed from Examples which will described hereinafter, it was surprisingly confirmed that the *Rhus verniciflua* extract according to the present invention exhibits superior anti-cancer effects particularly due to the resin thereof.

In investigation of anticancer effects through culture tests of cancer cells, the *Rhus verniciflua* extract, obtained according to the present invention, was also confirmed to have significantly superior growth inhibitory effects of cancer cells against colon cancer, liver cancer, uterine cancer, gastric cancer, rectal cancer and lung cancer. Further, the *Rhus verniciflua* extract of the present invention exhibited highly excellent therapeutic effects in the treatments of terminal cancer patients performed in oriental medicine hospitals.

Therefore, in accordance with another aspect of the present invention, there is provided an anti-cancer pharmaceutical composition, comprising (i) a therapeutically effective amount of a *Rhus verniciflua* extract as an active ingredient, and (ii) a pharmaceutically acceptable carrier, diluent or excipient, or any combination thereof.

The term "pharmaceutical composition" as used herein means a mixture of an extract of the present invention with other chemical components, such as diluents or carriers. The pharmaceutical composition facilitates administration of the compound to an organism. Various techniques of administering therapeutically active ingredient are known in the art and include, but are not limited to, oral, injection, aerosol, parenteral and topical administrations.

The term "therapeutically effective amount" as used herein means an amount of an active ingredient that is effective to relieve or reduce to some extent the symptoms associated with cancer in need of treatment, when the compound is administered. Thus, a therapeutically effective amount refers to an amount of the active ingredient which exhibits effects of (1) reversing the rate of progress of a cancer and metastasis thereof; (2) inhibiting to some extent further progress of the cancer and metastasis thereof; and/or, (3) relieving to some extent (or, preferably, eliminating) symptoms associated with the cancer.

The term "carrier" as used herein means a chemical compound that facilitates the incorporation of an active ingredient into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the active ingredient of interest as well as stabilize the biologically active form of the active ingredient. Salts dissolved in buffered solutions are utilized as diluents in the art. One commonly used buffer solution is phosphate buffered saline (PBS) because it mimics the ionic strength conditions of human body fluid. Since buffer salts can control the pH of a solution at low concentrations, a buffer diluent rarely modifies the biological activity of a compound.

The term "physiologically acceptable" defines a carrier or diluent that is not detrimental to the biological activity and physical properties of the active ingredient.

The extracts according to the present invention may be administered to a human patient per se, or in the form of pharmaceutical compositions in which they are mixed with other active ingredients, as in combination therapy, or suitable carriers or excipient(s). Techniques for formulation and administration of the compounds may be found in "Remington's Pharmaceutical Sciences," Mack Publishing Co., Easton, Pa., 18th edition, 1990.

a) Routes of Administration

Suitable routes of administration may, for example, include oral, intranasal, transmucosal, or intestinal administration; and parenteral delivery, including intramuscular, subcutaneous, intravenous, intramedullary injections, as well as intrathecal, direct intraventricular, intraperitoneal, or intraocular injections.

b) Compositions/Formulations

The pharmaceutical composition of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more pharmaceutically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as is suitable and understood in the art; e.g., in Remington's Pharmaceutical Sciences, above.

For injection, the agents of the present invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active ingredients with pharmaceutically acceptable carriers well known in the art. Such carriers enable the extract of the present invention to be formulated as tablet, pill, dragee, capsule, liquid, gel, syrup, slurry, suspension and the like, for oral ingestion by a patient. Pharmaceutical preparations for oral use can be obtained by mixing one or more excipients with the extract of the present invention, optionally grinding the resulting mixture, and processing the mixture of granules, after adding suitable auxiliaries, if desired, to obtain tablets or dragee cores. Suitable excipients may be fillers such as sugars, including lactose, sucrose, mannitol and sorbitol; and cellulose substances such as, for example, corn starch, wheat starch, rice starch, potato starch, gelatin, gum tragacanth, methyl cellulose, hydroxypropylmethyl-cellulose, sodium carboxymethyl cellulose, and/or polyvinylpyrrolidone (PVP). If desired, there may be added disintegrating agents such as cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally may include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate. In soft capsules, the active compounds may be dissolved or dispersed in suitable solvents, such as fatty acid, liquid paraffin, or liquid polyethylene glycols. In addition, stabilizers may also be added. All formulations for oral administration should be in dosage forms suitable for such administration.

For buccal administration, the compositions may take the form of tablets or lozenges formulated in a conventional manner.

For administration by inhalation, the extracts according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, e.g., gelatin for use in an inhaler or insufflator may be formulated containing a powdered mixture of the compound and a suitable powder base such as lactose or starch.

The extracts may also be formulated for parenteral administration by injection, e.g., by bolus injection or continuous infusion. Formulations for injection may be presented in unit dosage forms, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active ingredients in water-soluble form. Additionally, suspensions of the active ingredients may be prepared in the form of appropriate oily injection suspensions. Examples of suitable lipophilic solvents or vehicles include fatty oils such as sesame oil, or synthetic fatty acid esters such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, prior to use.

The active ingredient may also be formulated in rectal compositions such as suppositories or retention enemas, e.g., containing conventional suppository bases such as cocoa butter or other glycerides.

A pharmaceutical carrier for the extract according to the present invention is a co-solvent system comprising benzyl alcohol, a nonpolar surfactant, a water-miscible organic polymer, and an aqueous phase. The co-solvent system may be the VPD co-solvent system. VPD is a solution of 3% w/v benzyl alcohol, 85% w/v nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in an aqueous solution. This co-solvent system dissolves hydrophobic compounds well, and itself has minimal toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well-known examples of delivery vehicles or carriers for hydrophobic drugs. Certain organic solvents such as dimethylsulfoxide may also be employed, although usually at the cost of greater toxicity. Additionally, the active ingredients may be delivered using a sustained-release system, such as semipermeable matrices of solid hydrophobic polymers containing the therapeutic agent. Various sustained-release materials have been developed and are well-known to those skilled in the art. Sustained-release capsules may, depending on their chemical nature, release the compounds for from 2 or 3 weeks up to over 100 days. Depending on the chemical nature and the biological stability of the therapeutic reagent, additional strategies for protein stabilization may be employed.

c) Effective Dosage

Pharmaceutical compositions suitable for use in the present invention include compositions in which the active ingredients are contained in an amount effective to achieve its intended purpose. More specifically, a therapeutically effective amount means an amount of compound effective to prolong the survival of the subject being treated or prevent, alleviate or ameliorate symptoms of disease. Determination of a therapeutically effective amount is well within the capability of those skilled in the art, especially in light of the detailed disclosure provided herein.

For the extract used in the present invention, the therapeutically effective amount can be estimated initially from cell culture assays. For example, a dose can be formulated in animal models to achieve a circulating concentration range that includes the IC50 as determined in cell culture. Such information can be used to more accurately determine useful doses in humans.

The dosage may vary within the above range depending upon the dosage form employed and the route of administration utilized. The exact formulation, route of administration and dosage can be chosen by the attending physician in view of the patient's condition (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as needed.

In cases of local administration or selective uptake, the effective local concentration of the drug may not be related to plasma concentration.

The amount of composition administered will, of course, be dependent on the subject being treated, the subject's weight, the severity of the affliction, the manner of administration and the judgment of the prescribing physician.

EXAMPLES

Now, the present invention will be described in more detail with reference to the following examples. These examples are provided only for illustrating the present invention and should not be construed as limiting the scope and spirit of the present invention.

Example 1

Preparation of *Rhus verniciflua* Extract (Extract A)

10 kg of undried *Rhus verniciflua*, which was 10 years old and grown in Wonju, Korea, was subjected to a removal process of allergenicity according to the method disclosed in Korean Patent No. 0504160, processed into sawdust and dried. Two samples were prepared, each of which consisting of 100 g of dried sawdust. One sample is used for preparing an extract of the present invention (hereinafter, referred to as "Extract A"), and for comparison of the composition between two samples, the other sample is used for preparing a conventional water extract (hereinafter, referred to as "Extract B").

Extract A was prepared according to the following procedure.

1.3 L of water, which corresponds to 13-fold amount of the weight of *Rhus verniciflua* sawdust, was added to sawdust of undried *Rhus verniciflua*, and extraction was carried out at 100° C. and 1 atm for 6 hours. First extraction afforded 1.12 L of an extract, and 1.0 L of 45% (v/v) ethanol was added to the residues left after the first extraction, followed by extraction at 80° C. and 0.6 atm for 6 hours. Second extraction afforded 1.05 L of filtrate which was then mixed with the first extract. The mixture was filtered through a microfilter having a pore size of 1 μm to remove impurities. The thus-obtained filtrate was again filtered through an ultrafiltration membrane having a cut-off molecular weight of 500,000 to remove substances having a molecular weight of more than 500,000. The thus-obtained filtrate was recovered and concentrated to 20 mL by evaporation under vacuum at a temperature of 50° C., followed by lyophilization. The amount of solids removed while conducting the above process was 1.3 g. After drying, 8.8 g of brown powder was obtained as a product.

A colorless and transparent glass plate having a thickness of 1 mm was placed on the uppermost layer, and, spaced at a distance of 10 cm from the glass plate, black oak charcoal powder passing through a 100 mesh screen was spread to a thickness of 4 mm. The xylem of shade-dried *Rhus verniciflua* was finely ground into powder passing through a 50 mesh screen, which was then laid with a 1 mm thickness under the charcoal powder layer. Spaced at a distance of 5 cm from the *Rhus verniciflua* powder layer, a transparent polypropylene vinyl container, in which the *Rhus verniciflua* extract powder obtained as above was laid with a thickness of 2 cm. Then, oxygen was removed by purging with nitrogen in a 10-fold amount of the volume of the vinyl container, and the vinyl container was sealed after complete replacement of oxygen with nitrogen. Spaced at a distance of 10 cm from the glass plate of the uppermost layer, a 120 W far infrared-generation bulb was switch-on, and far infrared was irradiated for 8 hours. Upon irradiation of far infrared, a surface temperature of charcoal powder was about 80° C.

After irradiation with far infrared, the weight of *Rhus verniciflua* extract powder was measured to be 8.5 g, with about 3.4% decrease in weight as compared to no irradiation with far infrared. This extract was subsequently used in confirmation experiments of anti-cancer activity Comparative Example 1

Preparation of *Rhus verniciflua* Extract (Extract B)

For preparing Extract B, a water extraction process is first carried out in the same manner as in preparation of Extract A, by adding 1.3 L of water, which corresponds to 13-fold amount of *Rhus verniciflua* to be extracted, to sawdust of undried *Rhus verniciflua*, followed by extraction at 100° C. and 1 atm for 6 hours. First extraction afforded 1.12 L of an extract. 1 L of water was added again to the residues left after the first extraction, followed by extraction under the same conditions as above, thus obtaining 980 mL of an extract. Two extracts thus obtained were combined, concentrated in vacuo and lyophilized to prepare Extract B.

Contents of fustin, fisetin and resin in these extracts were analyzed. The results thus obtained are given in Table 1 below.

TABLE 1

Content analysis of fustin and fisetin

| Extracts | Fustin (%, w/w) | Fisetin (%, w/w) | Resin (% w/w) |
| --- | --- | --- | --- |
| Extract A | 23.1 | 9.2 | 39.4 |
| Extract B | 19.2 | 5.3 | 17.2 |

As can be seen from Table 1, the *Rhus verniciflua* extract (Extract A) in accordance with one embodiment of the present invention exhibited significant difference in contents of fustin, fisetin and resin, as compared to the water extract (Extract B).

Example 2

Toxicity and Safety Tests of *Rhus verniciflua* Extracts

In order to confirm whether Extract A prepared in Example 1 can be used as a drug, toxicity test was requested to perform by Biotoxtech (Korea), an institute approved by Korean Good Laboratory Practice (KGLP). The test results are given in Table 2 below.

TABLE 2

Results of toxicity tests on *Rhus verniciflua* extracts

| | Results |
| --- | --- |
| Dose-determination test of 4-week repeated dose oral administration in the rat | — |
| Toxicity test of 13-week repeated dose oral administration in the rat | No-observed-adverse-effect level (NOAEL), Male: 400 mg/kg; Female: 1600 mg/kg |
| Toxicity test of repeated oral administration with increasing doses in the beagle dog | No death and no significant changes found. Maximum dose ranged from 800 mg/kg to 1600 mg/kg |
| Toxicity test of 13-week repeated dose oral administration and 4-week recovery test in the beagle dog | Low dose: 43 mg/kg, and High dose: 450 mg/kg, as determined |
| Toxicity dose-determination test of oral administration on development of the embryos/fetuses in the rabbit | No death and no changes in body weight. No difference in weight of internal organs. No difference in weight of fetuses and survival rate |

As can be seen from Table 2, it was confirmed that the *Rhus verniciflua* extract in accordance with the present invention exhibited no toxicity problems upon using it as a drug.

Example 3

Test for Anti-Cancer Activity of *Rhus verniciflua* Extracts

In order to examine anti-cancer activity of the extract of the present invention (Extract A) prepared in Example 1 and the conventional water extract (Extract B), growth inhibitory effects of cancer cells were investigated on colon cancer, liver cancer, uterine cancer, gastric cancer, rectal cancer and lung cancer cells. Cancer cells used in this example and growth inhibitory effects are set forth in Table 3 below. For examination of anti-cancer activity, cancer cell lines (available from Korea Federation of Culture Collection: KFCC) were subcultured and $1\times10^6$ cells/ml were aliquoted to each well of a 24-well plate, followed by adding each 50 ppm of the *Rhus verniciflua* extract. Growth of cancer cells was compared therebetween.

TABLE 3

Anti-cancer activity of *Rhus verniciflua* extracts

| Cancers | Strains | Extract A - TGI (%) | Extract B - TGI (%) |
| --- | --- | --- | --- |
| Colon cancer | WiDr | 47 | 22 |
| Liver cancer | HEPG2 | 53 | 28 |
| Uterine cancer | He La | 75 | 31 |
| Gastric cancer | SNU-5 | 66 | 45 |
| Rectal cancer | SNU-1033 | 56 | 24 |
| Lung cancer | Calu-3 | 73 | 15 |

*TGI: Tumor Growth Inhibition

As can be seen from Table 3, Extract A in accordance with one embodiment of the present invention exhibited significantly high anti-cancer activity, as compared to Extract B.

Example 4

Comparison of Anti-Cancer Activity Between *Rhus verniciflua* Extracts Before and after Irradiation with Far-Infrared Anti-cancer activity between *Rhus verniciflua* extracts of the present invention before and after irradiation with far-infrared was compared. This is intended to observe a difference in terms of effects of far-infrared irradiation, taking into consideration difficulty to clearly describe physical properties of a far-infrared irradiation system or to quantify effects thereof. Similar to Example 3, anti-cancer activity was measured on Extract A prepared in Example 1, and an extract which was extracted according to the same procedure as in Example 1 but was not irradiated with far-infrared (Extract C), respectively. The results thus obtained are given in Table 4 below.

TABLE 4

Comparison of anti-cancer activity between *Rhus verniciflua* extracts before and after irradiation with far-infrared

|  | Extract A (before IR irradiation) TGI (%) | Extract C (after IR irradiation) TGI (%) |
| --- | --- | --- |
| Lung cancer | 33 | 73 |
| Uterine cancer | 48 | 75 |
| Liver cancer | 31 | 53 |

As can be seen from Table 4, irradiation with far-infrared resulted in 60 to 120% increase in anti-cancer activity Example 5

Confirmation of Allergen Removal

In order to confirm whether allergens were removed from *Rhus verniciflua* extracts according to the present invention, contents of urushiol, which is known to cause allergic reaction, were examined via HPLC, for Extract A of Example 1 and undried *Rhus verniciflua* extract (Extract D). Analysis of urushiol was carried out according to the method disclosed in Korean J. Medical Crop Sci., 10(4):288-93 (2002). The analysis results thus obtained are given in Table 5 below.

TABLE 5

Analysis results of urushiol content

| MW of Urushiol | Extract A | Extract D |
| --- | --- | --- |
| 314 | ND | 3.5% (w/w) |
| 316 | ND | 0.2% (w/w) |
| 318 | ND | 0.4% (w/w) |
| 320 | ND | 1.5% (w/w) |

*ND: Not Detected

As shown in Table 5, it can be seen that *Rhus verniciflua* extract obtained according to the method of the present invention was completely free of urushiol, known as an allergen.

Example 6

Anti-Cancer Activity of Resin

In order to confirm anti-cancer activity of resin components present in *Rhus verniciflua* extract according to the present invention, Extract A obtained in Example 1 was dissolved in water to remove water-soluble substances, and the remaining solids were dissolved in 95% (v/v) ethanol. The thus-obtained solution was concentrated in vacuo to thereby afford black resin components which were subjected to a confirmation test of anti-cancer activity. The results thus obtained are given in Table 6 below.

TABLE 6

Anti-cancer activity of resin: Comparison of TGI values

| Cancers | Strains | Resin 20 ppm | Resin 100 ppm |
| --- | --- | --- | --- |
| Colon cancer | WiDr | 55 | 77 |
| Liver cancer | HEPG2 | 67 | 87 |
| Uterine cancer | He La | 80 | 86 |
| Gastric cancer | SNU-5 | 56 | 64 |
| Rectal cancer | SNU-1033 | 88 | 93 |
| Lung cancer | Calu-3 | 75 | 92 |

*TGI: Tumor Growth Inhibition

As shown in Table 6, it can be seen that the resin exhibits significantly higher anti-cancer activity, as compared to the overall composition of *Rhus verniciflua* extract.

Example 7

Therapeutic Effects on Cancer Patients

Using *Rhus verniciflua* extract A, which was prepared in the same manner as in Example 1, therapeutic effects thereof were examined on terminal cancer patients in oriental medicine hospitals. Consequently, very highly outstanding therapeutic effects were observed. The results thus obtained are given in Table 7 below.

TABLE 7

| Cancers | 1-year survival rate (%) | 3-year survival rate (%) | 5-year survival rate (%) |
| --- | --- | --- | --- |
| Leukemia | 90.0 | 73.3 | 69.9 |
| Lymphoma | 90.9 | 81.8 | 81.8 |
| Lung cancer | 88.8 | 73.1 | 67.4 |
| Liver cancer | 78.2 | 67.1 | 56.1 |
| Gastric cancer | 68.6 | 64.1 | 60.4 |
| Prostate cancer | 55.2 | 34.4 | 19.4 |
| Colorectal cancer | 77.1 | 67.5 | 55.3 |
| Overall cancers (average survival rate) | 81.0 | 52.4 | 45.0 |

INDUSTRIAL APPLICABILITY

As apparent from the above description, *Rhus verniciflua* extracts prepared according to the method of the present invention exhibit superior anti-cancer activity and therefore can be effectively used to treat and prevent various kinds of cancers.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A process for preparation of a *Rhus verniciflua* extract, comprising:
   (a) extracting *Rhus verniciflua* with a soluble solvent, thereby obtaining an extract;
   (b) subjecting the extract to ultrafiltration to remove high-molecular weight substances, concentrating and drying the extract, thereby obtaining an extract powder; and
   (c) irradiating far-infrared the extract powder with a far-infrared treatment system comprised of a light source positioned at the uppermost part of the system; a light-absorbing/heat-emitting layer having a thickness of 0.5 to 1 cm, absorbing light from the light source and emitting heat, and being composed of charcoal powder having a 100-mesh size; a far-infrared radiating layer having a thickness of 0.5 to 1 mm, located underneath the light-absorbing/heat-emitting layer and composed of dried *Rhus verniciflua*; and a *Rhus verniciflua* extract powder layer having a thickness of 2 to 10 mm, located at a predetermined distance spaced away from the far-infrared radiating layer and sealed by a transparent substrate under inert atmosphere.

2. The process according to claim 1, wherein solvent extraction of step (a) includes adding an excessive amount of water as a first solvent to *Rhus verniciflua*, thereby obtaining a water extract; adding an excessive amount of dilute ethanol as a second solvent to the *Rhus verniciflua* residues left after the first extraction, thereby obtaining an ethanol extract; and combining the water extract and the ethanol extract to obtain a mixed extract.

3. The process according to claim 2, wherein water extraction is carried out at 60 to 110° C. for 3 to 24 hours by adding a 5 to 20-fold amount of water relative to weight of the *Rhus verniciflua*, and ethanol extraction is carried out at 60 to 70° C. for 3 to 10 hours by adding a 5 to 10-fold amount of dilute ethanol having a 40 to 50% (v/v) ethanol concentration relative to weight of the *Rhus verniciflua*.

4. The process according to claim 1, wherein microfiltration is additionally performed through a filter having a pore size of 0.45 μm, prior to the ultrafiltration of step (b).

5. The process according to claim 1, wherein a molecular weight cut-off value of a membrane used in ultrafiltration is more than 500,000.

* * * * *